US012672814B2

(12) United States Patent
Govari et al.

(10) Patent No.: US 12,672,814 B2
(45) Date of Patent: Jul. 7, 2026

(54) PROVIDING A BLOOD POOL DIRECTION VECTOR BASED ON MEASURED IMPEDANCES

(71) Applicant: BIOSENSE WEBSTER (ISRAEL) LTD., Yokneam (IL)

(72) Inventors: Assaf Govari, Haifa (IL); Vadim Gliner, Haifa (IL); Andres Claudio Altmann, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 185 days.

(21) Appl. No.: 18/389,953

(22) Filed: Dec. 20, 2023

(65) Prior Publication Data

US 2025/0204837 A1 Jun. 26, 2025

(51) Int. Cl.
| | |
|---|---|
| *A61B 5/367* | (2021.01) |
| *A61B 5/00* | (2006.01) |
| *A61B 5/287* | (2021.01) |
| *A61B 5/339* | (2021.01) |

(52) U.S. Cl.
CPC .............. *A61B 5/367* (2021.01); *A61B 5/287* (2021.01); *A61B 5/339* (2021.01); *A61B 5/6853* (2013.01); *A61B 5/6858* (2013.01); *A61B 2560/0468* (2013.01)

(58) Field of Classification Search
CPC ......... A61B 5/367; A61B 5/287; A61B 5/339; A61B 5/6853; A61B 5/6858; A61B 2560/0468; A61B 5/0537; A61B 5/0538; A61B 5/063; A61B 5/6869; A61B 5/6886; A61B 34/20; A61B 18/00; A61B 2018/00904; A61B 2034/2051

See application file for complete search history.

(56) References Cited

U.S. PATENT DOCUMENTS

| | | | |
|---|---|---|---|
| 5,391,199 A | 2/1995 | Ben-Haim | |
| 5,443,489 A | 8/1995 | Ben Haim | |
| 5,558,091 A | 9/1996 | Acker | |
| 6,172,499 B1 | 1/2001 | Ashe | |
| 6,239,724 B1 | 5/2001 | Doron | |
| 6,332,089 B1 | 12/2001 | Acker | |
| 6,484,118 B1 | 11/2002 | Govari | |
| 6,618,612 B1 | 9/2003 | Acker | |
| 6,690,963 B2 | 2/2004 | Ben Haim | |

(Continued)

FOREIGN PATENT DOCUMENTS

| | | | | | |
|---|---|---|---|---|---|
| AU | 2017212715 A1 | * | 5/2018 | ........... | A61B 5/6843 |
| IL | 284521 A | * | 1/2022 | ............. | G06N 3/045 |

OTHER PUBLICATIONS

Extended European Search Report received for EP Application No. 24221343.7, mailed on May 23, 2025, 8 pages.

*Primary Examiner* — Michael J Lau

(57) ABSTRACT

A method includes monitoring impedances of the plurality of the functional electrodes relative to a reference electrode while maneuvering a catheter within a cavity of an organ, the catheter comprising (i) a shaft having a distal end, and (ii) an expandable distal-end assembly coupled to the distal end of the shaft and comprising a plurality of functional electrodes. A direction vector is estimated from the monitored impedances, along which the catheter is free to advance within the cavity of the organ without obstruction by the tissue wall. The direction vector is displayed to a user.

14 Claims, 4 Drawing Sheets

(56) References Cited

U.S. PATENT DOCUMENTS

| | | | | |
|---|---|---|---|---|
| 6,788,967 | B2 | 9/2004 | Ben Haim | |
| 6,892,091 | B1 | 5/2005 | Ben Haim | |
| 7,263,397 | B2 * | 8/2007 | Hauck | A61B 5/065 |
| | | | | 600/509 |
| 7,536,218 | B2 | 5/2009 | Govari | |
| 7,756,576 | B2 | 7/2010 | Levin | |
| 7,848,787 | B2 | 12/2010 | Osadchy | |
| 7,869,865 | B2 | 1/2011 | Govari | |
| 7,925,348 | B1 * | 4/2011 | Bornzin | A61N 1/36521 |
| | | | | 607/23 |
| 8,456,182 | B2 | 6/2013 | Bar-Tal | |
| 8,801,693 | B2 * | 8/2014 | He | A61B 5/068 |
| | | | | 600/377 |
| 9,314,191 | B2 * | 4/2016 | Razavi | A61B 5/1107 |
| 10,350,002 | B2 * | 7/2019 | Terwey | A61B 18/1492 |
| 12,364,426 | B2 * | 7/2025 | Govari | A61B 5/367 |
| 2008/0200913 | A1 * | 8/2008 | Viswanathan | A61B 18/1492 |
| | | | | 606/41 |
| 2010/0130854 | A1 | 5/2010 | Shachar et al. | |
| 2020/0138333 | A1 * | 5/2020 | Govari | A61B 5/063 |
| 2022/0338783 | A1 | 10/2022 | Palti | |
| 2022/0409293 | A1 * | 12/2022 | Ben-Haim | A61B 5/367 |
| 2023/0112251 | A1 * | 4/2023 | Govari | A61B 5/6858 |
| | | | | 600/424 |
| 2023/0210437 | A1 * | 7/2023 | Beeckler | A61B 5/367 |
| | | | | 600/523 |

* cited by examiner

PROVIDING A BLOOD POOL DIRECTION VECTOR BASED ON MEASURED IMPEDANCES

FIELD OF THE DISCLOSURE

The present disclosure relates generally to anatomical mapping, and particularly to the improvement of cardiac electroanatomical (EA) mapping.

BACKGROUND OF THE DISCLOSURE

Techniques to assist in guiding an EA mapping catheter inside a cardiac chamber to acquire clinically relevant data for constructing an EA map of the cardiac chamber exist in patent literature. Such techniques may be accompanied by medical imaging such as fluoroscopy to assist the physician in navigating the catheter to an area of interest within the heart. Typically, it is desired to minimize the use of fluoroscopy to avoid exposing the patient as well as the medical staff to harmful radiation. While being very beneficial in cardiac treatment planning as well as in the treatment itself, maneuvering a catheter within a heart chamber to reach a region of interest requires a high degree of expertise from the physician who performs the procedure.

The present disclosure will be more fully understood from the following detailed description of the examples thereof, taken together with the drawings, in which:

DETAILED DESCRIPTION OF EXAMPLES

Overview

Wall tissue of a cardiac chamber can be electro-anatomically (EA) mapped using a catheter having multiple functional electrodes fitted at an expandable distal-end assembly of the catheter. In a mapping procedure in a cardiac chamber, the physician may manipulate an expanded distal-end assembly to have the electrodes contact chamber walls to acquire and/or apply electrical signals. The final EA map may include many anatomical details that are important to facilitate a treatment plan, such as, in case of a left atrium, the four pulmonary vein (PV) ostia and the lower left appendage.

However, at the early stages of a mapping procedure, the physician often has no information about where to direct the catheter to achieve efficient mapping. Only after some portion of the cardiac chamber surface is mapped can the physician make the mapping more efficient by accessing, in an informative way, the clinically relevant but less accessible locations in cardiac chambers, such as ostia, appendage, and valves. Even in later stages, it is often difficult to understand how to maneuver within the three-dimensional structure of the chamber. These difficult challenges during the beginning phase of an EA mapping can prolong the mapping procedure and make it more medically complicated for the patient. In some examples, a physician may want to reach a treatment area with minimal mapping performed during a treatment procedure with a treatment-type catheter.

Examples of the present disclosure described herein provide a technique that expedites the early stages of an EA mapping, by resolving, or bypassing, the above-described difficulty of efficiently mapping an unknown surface with a catheter.

In one example of the technique, a physician maneuvers an expanded distal-end assembly of the catheter within a cardiac chamber. The catheter comprises a distal-end assembly having a plurality of functional electrodes, e.g., a basket assembly or a balloon assembly with a plurality of electrodes thereon. While the catheter is being maneuvered, a processor monitors impedances of the plurality of the functional electrodes relative to a reference electrode. Using the monitored impedances, the processor estimates a blood pool direction vector along which the catheter is free to advance within the cardiac chamber. The processor displays the direction vector to a user as a respective blood direction arrow.

Figure 3:
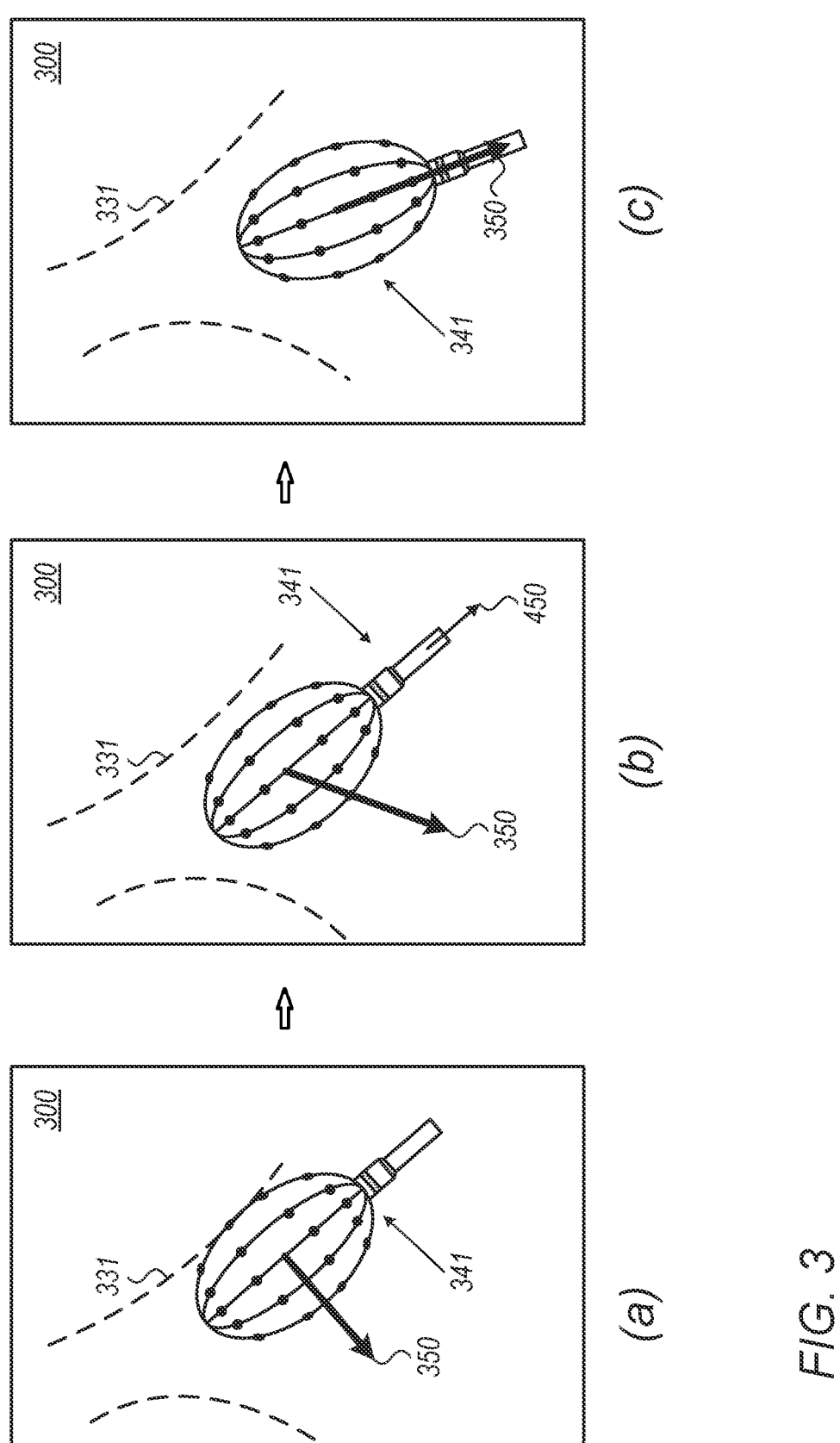
FIG. 3 is a schematic, pictorial illustration of a tissue wall proximity-based guiding scheme of a basket assembly of a catheter inside a left atrium of a patient, in accordance with an example of the present disclosure.

As noted above, the disclosed technique can overcome the difficulty of efficiently mapping an initially unknown tissue surface with a catheter. For example, the disclosed technique indicates the best approach to a landmark such as an ostium of a PV, a left atrial appendage (LAA), when the blood pool direction is aligned with the shaft of the catheter (e.g., by indicating that the direction arrow is aligned with a longitudinal axis icon of a virtual representation of the distal-end assembly), as Seen in FIG. 3.

While the method is applied to cardiac chambers it can be applied to another cavity of an organ by measuring cavity bulk and wall impedances.

To estimate the blood pool direction vector, in some examples the processor first identifies a maximum and minimum impedance for the patient and normalizes the range of impedances between the maximum and minimum. In addition to the variability between patients, the detected maximum and minimum values for each functional electrode depends on the distance between the functional electrode and reference electrode. These differences may be accounted for and a normalized range, e.g., 0-1 may be defined for each of the electrodes based on the maximum and minimum impedances identified.

In some examples, to estimate the blood pool direction vector, the processor relies on the known geometry of the expanded distal-end assembly. In some examples, a center point of the inner volume is computed and a vector extending from the center point to each of the electrodes is defined. In some example embodiments, deformation of the distal end assembly is tracked, and the center point of the inner volume is dynamically defined based on tracked deformation.

Magnitude of each vector is defined as a scaled value of the impedance sensed at the electrode. Typically, impedance increases as an electrode approaches the tissue. Since it is desired to indicate a direction away from the tissue and the impedance decreases as a function of distance from the tissue, the magnitude of each of the vectors may be defined as the maximum impedance level minus the instant impedance level. For example, for a range of impedance values normalized to be between 0-1, the magnitude of each vector may be one minus the normalized impedance value.

The processor converts each impedance of a functional electrode into a weighted vector, e.g., the magnitude of the vector is the weight of the vector, in the direction of the functional electrode from the common origin and sums the weighted vectors over all the functional electrodes. In the blood pool such a vector is fixed (e.g., close to zero for a fully symmetric arrangement of the functional electrodes) and can be assumed to be a property only of the assembly. Only when a portion of the functional electrodes of the assembly is in proximity with tissue wall does the sum of impedance-weighted vectors generate a distinct blood pool direction vector.

System Description

Figure 1:
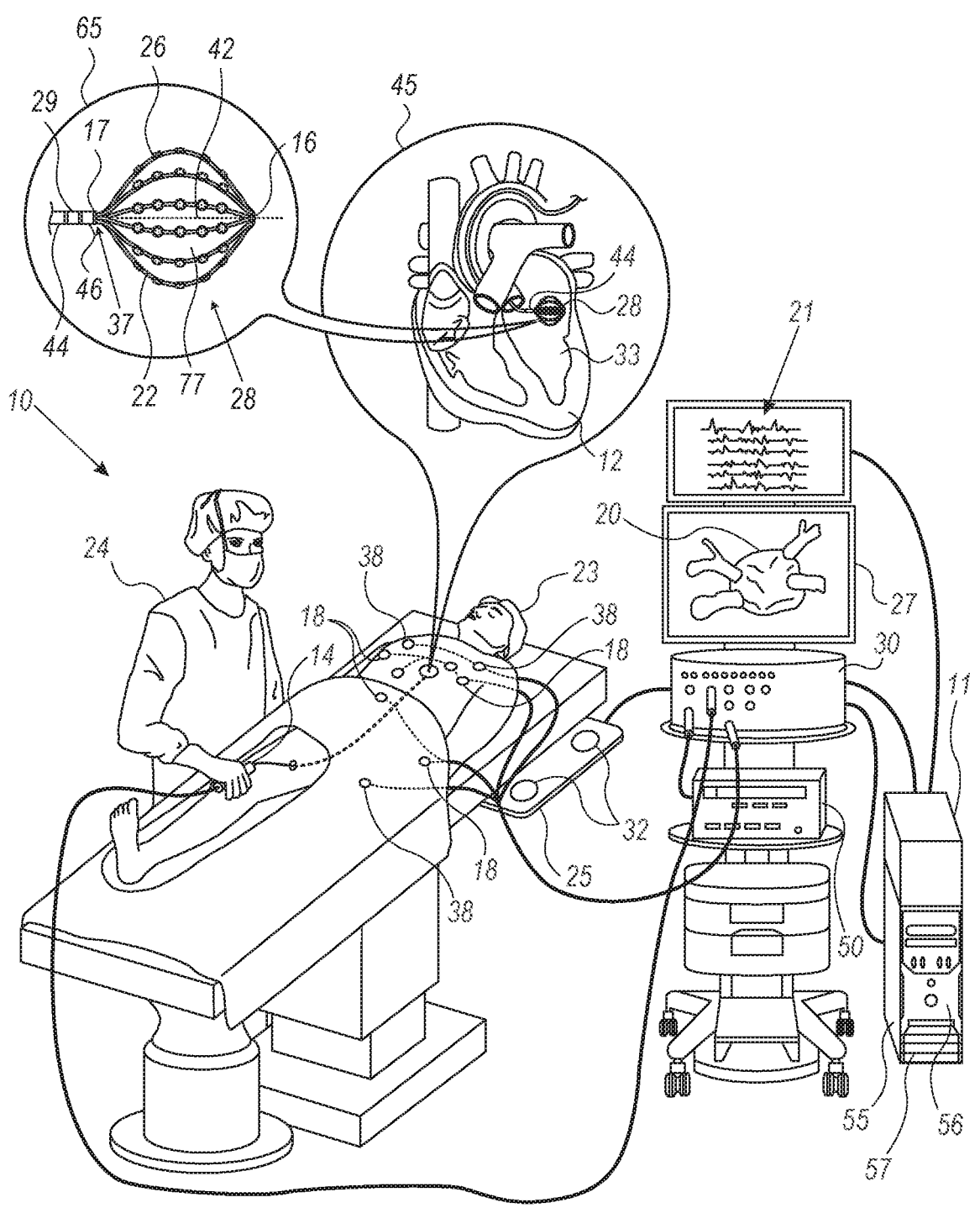
FIG. 1 is a schematic, pictorial illustration of a catheter-based electroanatomical (EA) mapping and ablation system, in accordance with an example of the present disclosure.

FIG. 1 is a schematic, pictorial illustration of a catheter-based electro-anatomical (EA) mapping and ablation system 10, in accordance with an example of the present disclosure. System 10 is configured to determine, e.g., prior to performing diagnostics and/or ablation, whether a given functional electrode 26 of a plurality of functional electrodes 26 of a basket catheter 14 has sufficient proximity to tissue or is immersed in blood pool 33 of a cardiac chamber.

System 10 includes one or more catheters which are inserted, by physician 24, through the percutaneously patient's vascular system into a chamber or vascular structure of a heart 12. Typically, a delivery sheath catheter is inserted into the left or right atrium near a desired location in heart 12. Thereafter, one or more catheters, in turn, can be inserted into the delivery sheath catheter to arrive at the desired location. The one or more catheters may include catheters dedicated for sensing intracardiac electrogram (IEGM) signals, catheters dedicated to ablating and/or catheters dedicated to both sensing and ablating. An example basket catheter 14 that is configured for sensing IEGM is illustrated herein. As seen in inset 45, physician 24 brings a basket type of expandable distal-end assembly 28 (also called hereinafter "expandable distal-end assembly 28") fitted on a shaft 44 of catheter 14 into proximity with the heart wall for sensing a target site in heart 12. For ablation, physician 24 similarly brings the distal end of an ablation catheter to a target site for ablating.

As seen in inset 65, catheter 14 is an exemplary catheter that includes one, and preferably multiple, functional electrodes 26 optionally distributed over a plurality of splines 22 at expandable distal-end assembly 28 and configured to sense IEGM signals. Catheter 14 additionally includes a proximal position sensor 29 (e.g., three axial sensor (TAS) 29 comprising three EMCs) embedded in a distal end 46 of shaft 44 near expandable distal end assembly 28, to track the position of the distal end of expandable distal end assembly 28. Optionally, and preferably, position sensor 29 is a magnetic-based position sensor that includes magnetic coils for sensing three-dimensional (3D) position. Distal end 46 of shaft 44 may comprise an amplifying circuit configured to amplify the output from the three EMCs of sensor 29.

Magnetic position sensor 29 is operated together with an external location pad 25 that includes a plurality of magnetic coils 32 configured to generate magnetic fields in a predefined working volume. Using the operation with external location pad 25 (each EMC using different frequency), the processor can determine the position of each EMC 29 on a coordinate system of the position tracking system.

Details of the magnetic-based position sensing technology are described in U.S. Pat. Nos. 5,5391, 199; 5,443,489; 5,558,091; 6,172, 499; 6, 239, 724; 6,332,089; 6,484,118; 6,618,612; 6,690, 963; 6,788, 967; 6,892,091.

System 10 includes one or more electrode patches 38 positioned for skin contact on patient 23 to establish a location reference for location pad 25 as well as impedance-based tracking of functional electrodes 26. For impedance-based tracking, electrical current is directed toward electrodes 26 and sensed at electrode skin patches 38, such that the location of each electrode can be triangulated via electrode patches 38. Real-time orientation of expandable distal end assembly 28 of catheter 14 can be calculated from tracked locations of electrodes 26. This relative orientation is manifested by an angle formed between distal end 46 and a longitudinal axis 42 of expandable assembly 28 (to a distal edge 16 of the assembly).

Details of the impedance-based location tracking technology are described in US Patent Nos. 7, 536, 218; 7,756,576; 7,848,787; 7,869,865; and 8,456,182.

Catheter 14 is configured to acquire electrical signals indicative of proximity of any given functional electrode 26 to the tissue wall of heart 12. To this end, a signal generator 35 is configured to generate an AC signal between a reference ring electrode 17 and each of the functional electrodes 26. The processor measures corresponding impedances between each functional electrode 26 and reference ring electrode 17 located on a base 37 of the expandable distal-end assembly 28 externally to an inner volume 77 defined by the splines of assembly 28. An electrical path between each functional electrode 26, and an electrical path between reference ring electrode 17 and assembly 28, improves the sensitivity of the measurement to tissue proximity. Reference ring electrode 17 is positioned on a base of the assembly 28 in a place that prevents contact with the tissue wall while the distal end assembly 28 is in an expanded state, as further described in FIG. 2.

A recorder 11 displays electrograms 21 captured with body surface ECG electrodes 18 and intracardiac electrograms (IEGM) captured with functional electrodes 26 of catheter 14. Recorder 11 may include pacing capability for pacing the heart rhythm and/or may be electrically connected to a standalone pacer.

System 10 may include an ablation energy generator 50 that is adapted to conduct ablative energy to a subset of the plurality of electrodes 26 at the distal assembly 28 of catheter 14 configured for ablating. Energy produced by ablation energy generator 50 may include, but is not limited to, radiofrequency (RF) energy or pulsed-field ablation (PFA) energy, including monopolar or bipolar high-voltage DC pulses that may be used to effect irreversible electroporation (IRE), or combinations thereof.

Patient interface unit (PIU) 30 is configured to establish electrical communication between catheters, electrophysiological equipment, a power supply and workstation 55 for controlling the operation of system 10. Electrophysiological equipment of system 10 may include, for example, multiple catheters, location pad 25, body surface ECG electrodes 18, electrode patches 38, ablation energy generator 50, and recorder 11. Optionally, and preferably, PIU 30 additionally includes processing capability for implementing real-time computations of catheter locations and for performing ECG calculations.

Workstation 55 includes memory 57, processor unit 56 with memory or storage with appropriate operating software loaded therein, and user interface capability. Workstation 55 may provide multiple functions, optionally including (i)

modeling endocardial anatomy in three-dimensions (3D) and rendering the model or anatomical map 20 for display on a display device 27, (ii) displaying on display device 27 activation sequences (or other data) compiled from recorded electrograms 21 in representative visual indicia or imagery superimposed on the rendered anatomical map 20, (iii) displaying real-time location and orientation of multiple catheters within the heart chamber, and (iv) displaying sites of interest, such as places where ablation energy has been applied, on display device 27. One commercial product embodying elements of system 10 is available as the CARTO™ 3 System, available from Biosense Webster, Inc., 31A Technology Drive, Irvine, CA 92618.

While FIG. 1 describes a basket assembly, the disclosed technique can be applied, mutatis mutandis, to an expandable balloon assembly having an expandable membrane, wherein the functional electrodes are disposed over the membrane.

Estimation of a Blood Pool Direction for an Expandable Assembly

Figure 2:
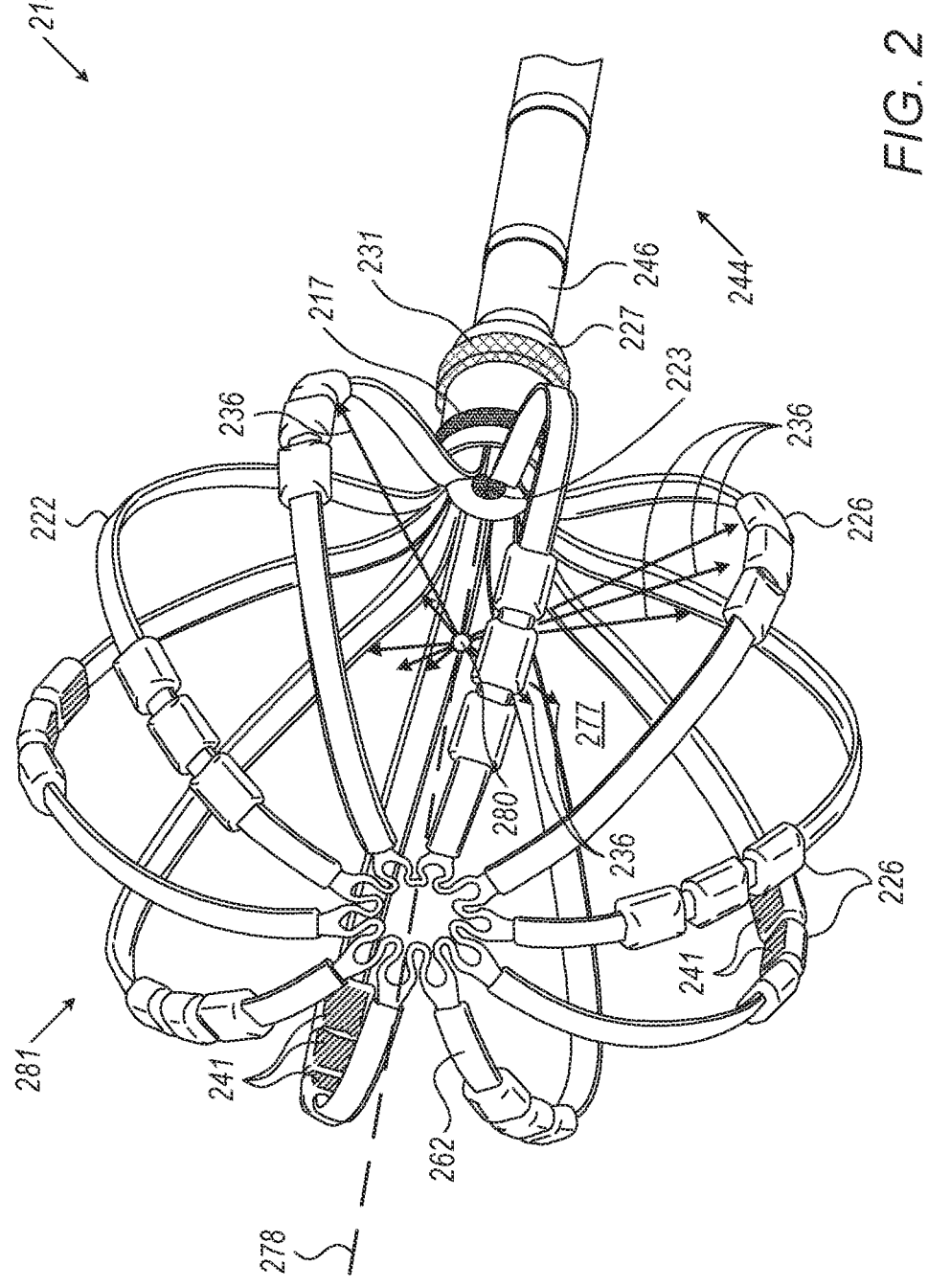
FIG. 2 is a schematic, pictorial illustration of a basket assembly configured to acquire electrical measurements to determine a blood pool direction of the assembly to a cardiac chamber tissue wall, in accordance with an example of the present disclosure.

FIG. 2 is a schematic, pictorial illustration of a basket assembly 281 configured to acquire electrical measurements to determine a proximity vector 215 of the assembly 281 to a cardiac chamber tissue wall, in accordance with an example of the present disclosure.

Basket assembly 281 can be used to implement basket assembly 28 of FIG. 1 above. As seen, assembly 281 is part of a catheter 214 further comprising a shaft 244 having a distal end 246. Distal-end assembly 228 includes a proximal base 227 configured to couple the assembly to a distal end 246 of the shaft 244. A distal axis 278 of the assembly is defined by a longitudinal axis of distal end 246 of the shaft 244.

Basket assembly 281 is realized as an expandable frame comprising multiple splines 222, wherein the functional electrodes 226 are coupled to the splines. Splines 22 are each electrically insulated from the environment over most of their area by an insulation layer 262.

When expanded, as shown in FIG. 3, the expandable distal-end assembly 281 defines an inner volume 277. At the base of the assembly, inside volume 277, a far-field electrode 223 is used to remove far-field signals from IEGM signals acquired by electrodes 226.

The plurality of functional electrodes 226 are at least partially external to the inner volume and are configured to be placed in contact with wall tissue of the cardiac chamber. A reference ring electrode 217 (such as ring electrode 17 of FIG. 1), is located on proximal base 227 of the expandable distal-end assembly 281 and externally to the inner volume 277. The ring-shaped electrode 217 over base 227 is positioned to avoid tissue wall contact while the distal end assembly 281 is in an expanded state.

In the example of FIG. 2, reference ring electrode 217 is a ring fitted on an external perimeter of the proximal base section 227. Reference ring electrode 217 may be disposed over an insulating layer (not shown), for example when base section 227 is electrically conductive (e.g., made of nitinol).

The proximal base section 227 further comprises a mechanical guard ring 231 that protrudes outward from the proximal base, i.e., further than reference electrode 217, to prevent reference electrode 217 from contacting tissue wall. Further improvement of measurement accuracy can be achieved by applying an inner electrical insulation coating 241 to electrode 226 so that the electrode portion in the blood is minimized upon contact with tissue. Coating 241 may be a type of polymer or an additional dielectric layer (e.g., silicon nitride).

Processor 56 receives impedance signals between each of electrodes 226 and reference electrode 217. As the catheter is moved in the blood pool, and also comes in contact with tissue, the processor obtains a range of impedances with a magnitude range between a minimal value $R_B$ from electrodes 226 in the blood pool and a maximal value $R_T$ from electrodes 226 in sufficient proximity or contact with tissue.

The processor defines a weight $f_j$ of an electrode direction unit vector $v_j$, for an electrode having an impedance R as $f_j=(R_T-R)/(R_T-R_B)$. As seen, weight $f_j$ is the magnitude of the unit vector $v_j$ and is equal to the impedance value after normalizing the range, e.g., a value between zero and one. For simplicity, all vectors $v_j$ are assumed to have the same unit magnitude (i.e., assuming a sphere-shaped expanded distal end assembly normalized to a unit sphere). The weight $f_j$ can have any value between 0 and 1.

An electrode immersed in blood has $f_j=1$ while an electrode in sufficient proximity with tissue has $f_j=0$. Some impedance-weighted vectors $f_j v_j$, 236, that originate from the assembly center 280, are shown by way of example.

The blood direction vector B, represented by an arrow 350 in FIG. 3, is given by a weighted sum on all vectors $v_j$:

$$B = -\sum_j (1 - f_j) v_j$$

While FIG. 2 describes a basket assembly, the disclosed technique can be applied, mutatis mutandis, to an expandable balloon assembly having an expandable membrane, wherein the functional electrodes are disposed over the membrane.

Providing a Blood Pool Direction Vector Based on Measured Impedances

FIG. 3 is a schematic, pictorial illustration of a proximity-based guiding scheme of basket catheter 214 inside a left atrium of a patient, in accordance with an example of the present disclosure. The figure shows output of the scheme in a window 300, presented to physician 24, for example, on display 27. Window 300 presents, in real time, an early phase of the EA mapping, when little of the left atrium wall is already EA mapped. Window 300 shows the EA-mapped tissue wall portion 331, an icon 341 of the distal end assembly 281, and arrow 350 indicating the blood pool direction (as found by B), where arrow 350 indicates to the physician 24 a direction at which distal end assembly 281 may be advanced without engaging the tissue wall.

By way of example, there exploration stages of the distal end assembly are represented in three windows 300, (a), (b) and (c). Each window of windows (a), (b) and (c) provides the physician with real-time advice on the blood pool direction 350 to move the catheter allowing the physician to advance more quickly during the exploratory phase of the EA mapping procedure, e.g., the expansion of rendering 331 into a more clinically meaningful EA map portion.

As indicated by the arrows, window (c) may represent an advanced stage of exploration compared to that seen in window (b). Similarly, window (b) may represent an advanced stage of exploration compared to that seen in window (a). FIG. 3 (c) indicates to a user that the best approach for an ostium of a PV was achieved when the blood pool direction 350 is aligned with the shaft of the catheter (e.g. by indicating when the direction arrow 350 is aligned, up to a predefined tolerance, with a longitudinal axis icon 450 of the distal-end assembly icon 341 (e.g., a virtual representation 341)).

Once EA mapping has been gathered on a sufficient number of anatomical landmarks (e.g., an ostium of a pulmonary vein), the work of the physician to EA map the cardiac chamber becomes easier.

Method of Providing a Blood Pool Direction Vector Based on Measured Impedances

Figure 4:
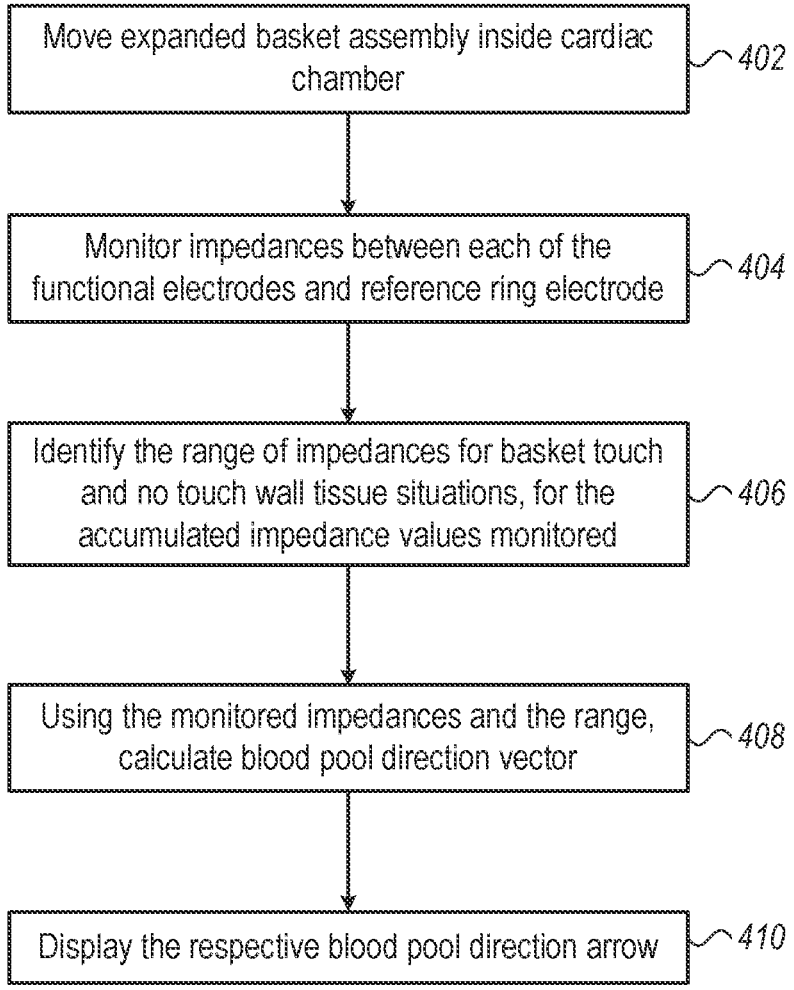
FIG. 4 is a flow chart that schematically illustrates a method and algorithm to estimate and present a blood pool direction vector that is based on measured impedances of functional electrodes, in accordance with an example of the present disclosure.

FIG. 4 is a flow chart that schematically illustrates a method and algorithm to estimate and present a blood pool direction arrow 350, based on measured impedances of functional electrodes, in accordance with an example of the present disclosure. The algorithm, according to the present embodiment, carries out a process that begins with moving the expanded basket assembly 281 inside a cardiac chamber of heart 12, at a basket moving step 402.

While the basket is moved, at baseline impedances monitoring step 404, system 10 monitors impedances between each of functional electrodes 226 and reference ring electrode 217.

At impedance range identification step 406, as the basket occasionally contacts cardiac chamber tissue wall, the processor identifies the range of impedances for touch and no touch for the accumulated impedance values monitored. A dedicated range is defined for each of the electrodes as the range is a function of distance between the functional electrode and the reference electrode. However, the range for individual electrodes can be inferred from a conglomerate output from all the functional electrodes 226 by compensating for different distances between each of functional electrodes 226 and the reference electrode.

Using the monitored impedance and its identified range, the processor calculates the blood pool direction vector B 350, at blood pool direction vector calculation step 408.

Finally, at a direction arrow displaying step 410, the processor displays the respective blood pool direction arrow 350 in association with a rendering of the distal end assembly, e.g., arrow 350 on window 300.

The example flow chart shown in FIG. 4 is chosen purely for the sake of conceptual clarity. The present embodiment also comprises additional steps of the algorithm, such as acquiring intra-cardiac electrocardiograms, which have been omitted from the disclosure herein purposely to provide a more simplified flow chart.

EXAMPLES

Example 1

A method includes monitoring impedances of a plurality of the functional electrodes (26) relative to a reference electrode (17) while maneuvering a catheter (14) within a cavity of an organ (12), the catheter comprising (i) a shaft (44) having a distal end (46), and (ii) an expandable distal-end assembly (28) coupled to the distal end (46) of the shaft (44) and comprising the plurality of functional electrodes. A direction vector is estimated from the monitored impedances, along which the catheter is free to advance within the cavity of the organ without obstruction by a tissue wall of the cavity. The direction vector is displayed (300) to a user.

Example 2

The method according to example 1, wherein estimating the direction vector comprises estimating, from the monitored impedances, a blood pool direction (350).

Example 3

The method according to any of examples 1 and 2, wherein estimating the blood pool direction vector comprises, based on a known geometry of the distal-end assembly (28), converting each impedance of a functional electrode (26) into a weighted vector in a direction of the functional electrode, and summing the weighted vectors over all the functional electrodes (26).

Example 4

The method according to any of examples 1 through 3, wherein converting each impedance of a functional electrode (26) into a weighted vector in the direction of the functional electrode (26) comprises (i) identifying a range of impedances for accumulated impedance values, and (ii) normalizing each impedance within the range according to the range to be a weight of the respective weighted vector.

Example 5

The method according to any of examples 1 through 4, wherein converting each impedance of a functional electrode (26) into a weighted vector comprises calculating a weight by normalizing the impedance with respect to the range to a value between zero and one.

Example 6

The method according to any of examples 1 through 5, wherein displaying (300) the direction vector comprises presenting a direction arrow (350) on a virtual representation of the distal-end assembly (341) shown on an electroanatomical (EA) map generated using EA signals from the functional electrodes.

Example 7

The method according to any of examples 1 through 6, wherein displaying the direction vector comprises indicating that the direction arrow (350) is aligned with a longitudinal axis icon (450) of the virtual representation (341) of the distal-end assembly (28).

Example 8

The method according to any of examples 1 through 7, wherein the distal-end assembly is one of a basket assembly (281) and a balloon assembly.

Example 9

A system includes an interface (30) and a processor (56). The interface (30) is configured to monitor impedances of the plurality of the functional electrodes (26) relative to a reference electrode (17) while maneuvering a catheter within a cavity of an organ (12), the catheter comprising (i) a shaft (44) having a distal end (46), and (ii) an expandable distal-end assembly (28) coupled to the distal end of the shaft and comprising a plurality of functional electrodes (26). The processor (56) is configured to (i) estimate from the monitored impedances a direction vector along which the catheter is free to advance within the cavity of the organ without obstruction by the tissue wall, and (ii) display (300) the direction vector to a user.

Although the examples described herein mainly address cardiac diagnostic applications, the methods and systems described herein can also be used in other medical applications.

It will be appreciated that the examples described above are cited by way of example, and that the present disclosure is not limited to what has been particularly shown and described hereinabove. Rather, the scope of the present disclosure includes both combinations and sub-combinations of the various features described hereinabove, as well as variations and modifications thereof which would occur to persons skilled in the art upon reading the foregoing description and which are not disclosed in the prior art.

The invention claimed is:

1. A method, comprising: monitoring impedances of each of the plurality of a functional electrodes relative to a reference electrode while maneuvering a catheter within a cavity of an organ, the catheter comprising (i) a shaft having a distal end, (ii) the reference electrode fixed to the distal end of the shaft and (iii) an expandable distal-end assembly coupled to the distal end of the shaft and comprising the plurality of functional electrodes; estimating from the monitored impedances a direction vector along which the catheter is free to advance within the cavity of the organ without obstruction by a tissue wall of the cavity, wherein the estimating comprises, based on a known geometry of the distal-end assembly, converting each impedance of a functional electrode into a weighted vector in a direction of the functional electrode, and summing the weighted vectors over all the functional electrodes, wherein the magnitude and the direction of the direction vector is defined by the summing; and displaying the direction vector to a user.

2. The method according to claim 1, wherein estimating the direction vector comprises estimating, from the monitored impedances, a blood pool direction.

3. The method according to claim 1, wherein converting each impedance of a functional electrode into a weighted vector in the direction of the functional electrode comprises: identifying a range of impedances for accumulated impedance values; and normalizing each impedance within the range according to the range to be a weight of the respective weighted vector.

4. The method according to claim 3, wherein converting each impedance of a functional electrode into a weighted vector comprises calculating a weight by normalizing the impedance with respect to the range to a value between zero and one.

5. The method according to claim 1, wherein displaying the direction vector comprises presenting a direction arrow on a virtual representation of the distal-end assembly shown on an electroanatomical (EA) map generated using EA signals from the functional electrodes.

6. The method according to claim 5, wherein displaying the direction vector comprises indicating that the direction arrow is aligned with a longitudinal axis icon of the virtual representation of the distal-end assembly.

7. The method according to claim 1, wherein the distal-end assembly is one of a basket assembly and a balloon assembly.

8. A system, comprising: an interface configured to monitor impedances of a plurality of the functional electrodes relative to a reference electrode while maneuvering a catheter within a cavity of an organ, the catheter comprising (i) a shaft having a distal end, (ii) the reference electrode fixed to the distal end of the shaft and (iii) an expandable distal-end assembly coupled to the distal end of the shaft and comprising the plurality of functional electrodes; and a processor, which is configured to: estimate from the monitored impedances a direction vector along which the catheter is free to advance within the cavity of the organ without obstruction by a tissue wall of the cavity, wherein the processor is configured to estimate the blood pool direction vector by, based on a known geometry of the distal-end assembly, converting each impedance of a functional electrode into a weighted vector in a direction of the functional electrode, and summing the weighted vectors over all the functional electrodes, wherein the magnitude and the direction of the direction vector is defined by the summing; and display the direction vector to a user.

9. The system according to claim 8, wherein the processor is configured to estimate the direction vector by estimating, from the monitored impedances, a blood pool direction.

10. The system according to claim 8, wherein the processor is configured to convert each impedance of a functional electrode into a weighted vector in the direction of the functional electrode by: identifying a range of impedances for accumulated impedance values; and normalizing each impedance within the range according to the range to be a weight of the respective weighted vector.

11. The system according to claim 10, wherein the processor is configured to convert each impedance of a functional electrode into a weighted vector by calculating a weight by normalizing the impedance with respect to the range to a value between zero and one.

12. The system according to claim 8, wherein the processor is configured to display the direction vector by presenting a direction arrow on a virtual representation of the distal-end assembly shown on an EA map generated using EA signals from the functional electrodes.

13. The system according to claim 12, wherein the processor is configured to display the direction vector by indicating that the direction arrow is aligned with a longitudinal axis icon of the virtual representation of the distal-end assembly.

14. The system according to claim 8, wherein the distal-end assembly is one of a basket assembly and a balloon assembly.

* * * * *